United States Patent
Ahearn et al.

(10) Patent No.: US 12,130,288 B2
(45) Date of Patent: Oct. 29, 2024

(54) METHODS AND SYSTEMS USING C4 GENE COPY NUMBER AND CELL-BOUND COMPLEMENT ACTIVATION PRODUCTS FOR IDENTIFICATION OF LUPUS AND PRE-LUPUS

(71) Applicants: Allegheny Singer Research Institute, Pittsburgh, PA (US); Research Institute At Nationwide Children's Hospital, Columbus, OH (US)

(72) Inventors: Joseph M. Ahearn, Wexford, PA (US); Chau-Ching Liu, Pittsburgh, PA (US); Susan M. Manzi, Wexford, PA (US); C. Yung Yu, Columbus, OH (US)

(73) Assignees: Allegheny Singer Research Institute, Pittsburgh, PA (US); Research Institute At Nationwide Children's Hospital, Columbus, OH (US)

(*) Notice: Subject to any disclaimer, the term of this patent is extended or adjusted under 35 U.S.C. 154(b) by 976 days.

(21) Appl. No.: 16/303,345

(22) PCT Filed: May 24, 2017

(86) PCT No.: PCT/US2017/034315
§ 371 (c)(1),
(2) Date: Nov. 20, 2018

(87) PCT Pub. No.: WO2017/205532
PCT Pub. Date: Nov. 30, 2017

(65) Prior Publication Data
US 2019/0302112 A1   Oct. 3, 2019

Related U.S. Application Data

(60) Provisional application No. 62/340,780, filed on May 24, 2016.

(51) Int. Cl.
| | | |
|---|---|---|
| *C12Q 1/68* | (2018.01) | |
| *C12Q 1/6883* | (2018.01) | |
| *G01N 33/564* | (2006.01) | |
| *G16B 20/10* | (2019.01) | |
| *G16H 10/40* | (2018.01) | |
| *G16H 15/00* | (2018.01) | |
| *G16H 50/30* | (2018.01) | |

(52) U.S. Cl.
CPC ............ *G01N 33/564* (2013.01); *C12Q 1/68* (2013.01); *C12Q 1/6883* (2013.01); *G16B 20/10* (2019.02); *G16H 10/40* (2018.01); *G16H 15/00* (2018.01); *G16H 50/30* (2018.01); *C12Q 2600/158* (2013.01); *G01N 2800/104* (2013.01); *G01N 2800/50* (2013.01)

(58) Field of Classification Search
None
See application file for complete search history.

(56) References Cited

U.S. PATENT DOCUMENTS

| | | | | |
|---|---|---|---|---|
| 9,495,517 | B2* | 11/2016 | Ahearn | C12Q 1/6883 |
| 9,863,946 | B2* | 1/2018 | Ahearn | C12Q 1/6883 |
| 2017/0067893 | A1 | 3/2017 | Ahearn et al. | |

FOREIGN PATENT DOCUMENTS

| | | | | |
|---|---|---|---|---|
| WO | WO-2014124098 A1 * | 8/2014 | | C12Q 1/6883 |
| WO | 2014151238 A1 | 9/2014 | | |
| WO | 2016023006 A1 | 2/2016 | | |

OTHER PUBLICATIONS

Wallace et al., "Systemic lupus erythematosus and primary fibromyalgia can be distinguished by testing for cell-bound complement activation products", (2016) Lupus Science & Medicine 3:1-7 (Year: 2016).*

Bhattad, Sagar, "Early Complement Component Deficiency in a Single-Centre Cohort of Pediatric Onset Lupus", Journal of Clinical Immunology, vol. 35, No. 8, Nov. 13, 2015, pp. 777-785.

Wu, Y L et al., "Molecular basis of complete complement C4 deficiency in two North-African families with systemic lupus erythematosus", Genes and Immunity, vol. 10, No. 5, Mar. 12, 2009, pp. 433-445.

Saxena, Kapil et al., "Great genotypic and phenotypic diversities associated with copy-number variations of complement C4 and RP-C4-CYP21-TNX (RCCX) modules: A comparison of Asian-Indian and European American populations", Molecular Immunology, Pergamon, GB, vol. 46, No. 7, Apr. 1, 2009, pp. 1289-1303.

Kalunian, Kenneth C. et al., "Measurement of Cell-Bound Complement Activation Products Enhances Diagnostic Performance in System Lupus Erythematosus", Arthritis & Rheumatism, vol. 64, No. 12, Dec. 1, 2012, pp. 4040-4047.

Ramsey-Goldman, Rosalind et al., "Cell-bound complement activation products in SLE", Lupus Science & Medicine, vol. 4, No. 1, Aug. 1, 2017.

Mossell, James et al., "The Avise Lupus Test and Cell-bound Complement Activation Products Aid the Diagnosis of Systemic Lupus Erythematosus", The Open Rheumatology Journal, vol. 10, No. 1, Oct. 31, 2016, pp. 71-80.

Hahn, Bevra H. et al., American College of Rheumatology Guidelines for Screening, Treatment, and Management of Lupus Nephritis, Arthritis Care & Research, vol. 64, No. 6, Jun. 2012, pp. 797-808.

Raj, Naveen et al., Can Cell Bound Complement Activation Products Predict Inherited Complement Deficiency in Systemic Lupus Erythematosus?, Hindawi Publishing Corporation, Case Reports in Rheumatology, vol. 2016, Article ID 8219317, 4 pages.

Yang, Yan et al., Gene Copy-Number Variation and Associated Polymorphisms of Complement Component C4 in Human Systemic Lupus Erythematosus (SLE): Low Copy Number Is a Risk Factor for and High Copy Number is a Protective Factor against SLE Susceptibility in European Americans, The American Journal of Human Genetics, vol. 80, Jun. 2008, pp. 1037-1054.

(Continued)

*Primary Examiner* — Jehanne S Sitton
(74) *Attorney, Agent, or Firm* — Fox Rothschild LLP

(57) ABSTRACT

Cell-bound complement activation product (CB-CAP) profiling is combined with determination of C4 gene copy number as biomarkers for lupus and/or pre-lupus diagnosis and monitoring.

11 Claims, 9 Drawing Sheets

(56) References Cited

OTHER PUBLICATIONS

Fernando, Michelle M.A. et al., Assessment of Complement C4 Gene Copy Number Using the Paralog Ration Test, Europe PMC Funders Group, Hum Mutat. Author manuscript, PMC Feb. 8, 2013.
International Search Report and Written Opinion mailed Aug. 25, 2017 in Application No. PCT/US17/34315.
Liu, C. et al., The Search for Lupus Biomarkers, Best Pract Res Clin Rheumatol. Aug. 2009 ; 23(4): 507-523.

\* cited by examiner

METHODS AND SYSTEMS USING C4 GENE COPY NUMBER AND CELL-BOUND COMPLEMENT ACTIVATION PRODUCTS FOR IDENTIFICATION OF LUPUS AND PRE-LUPUS

I. CROSS-REFERENCE TO RELATED APPLICATIONS

This application is a national stage application of, and claims priority to International Patent Application No. PCT/US2017/034315, filed May 24, 2017, which claims priority to U.S. Provisional Patent No. 62/340,780, filed May 24, 2016, titled "C4 Gene Copy Number and Cell-Bound Complement Activation Products as Companion Biomarkers for Diagnosis, Monitoring, and Stratification of Lupus and Pre-Lupus," the disclosure of which is incorporated by reference herein in its entirety.

BACKGROUND

Systemic Lupus Erythematosus (SLE), commonly referred to as lupus, is the prototypic autoimmune disease characterized by immune dysregulation (e.g., autoantibody and immune complex formation, complement activation, lymphocyte hyperreactivity, and skewed cytokine production) and consequent inflammatory tissue injury. The clinical manifestations of lupus are heterogeneous, ranging from subtle symptoms to fatal disease, and may involve any tissue and organ of the patient. Although lupus primarily affects women of reproductive age, it is a disease of any age and gender. The onset of lupus may be insidious with symptoms such as fever, joint pain, and fatigue, which are common in non-lupus diseases. Lupus is also characterized by periodic aggravation (flares) and remission of the disease. Meanwhile, serious organ damage may occur and go unrecognized since the early stage of the disease.

Diagnosing lupus remains a major clinical challenge. Although several blood tests are commonly used to aid physicians in making a diagnosis of lupus, no single test is sufficiently sensitive and specific for determining whether a patient has lupus. The typical patient with lupus requires four different physicians over a period of five years to be diagnosed in an accurate manner.

The non-specific symptoms and blood tests may sometimes be overlooked or overemphasized, resulting in underdiagnosis or overdiagnosis. Underdiagnosis and delayed diagnosis undoubtedly may lead to increased morbidity and mortality of patients who actually have lupus. Conversely, overdiagnosis of lupus may result in unnecessary exposure to toxic medications, which can be costly and have significant side effects in patients who do not have lupus. Therefore, a timely and precise diagnosis has significant impact on not only the physical well-being of patients but also on the economic well-being of the health care system.

Monitoring lupus is also a major clinical challenge as the course of the disease is characterized by a pattern of unpredictable flares and remissions. Delayed detection of a flare results in tissue inflammation and possible irreversible damage. Unnecessary delays in decreasing medications following resolution of a flare can result in an increased risk of side effects from toxic therapies used to treat lupus.

The heterogeneity of lupus also poses a major clinical challenge. Every organ system in the body, including but not limited to the skin, joints, heart, brain, lungs, and kidneys can be affected by the disease but there is no way to predict which patient is at risk for involvement of any specific organ system. Early identification of patients who are at risk of major complication of lupus such heart attack, stroke or kidney failure could result in earlier institution of preventive and therapeutic measures leading to decreased morbidity and mortality.

SUMMARY

This document identifies, in certain aspects, methods and systems in which cell-bound complement activation product (CB-CAP) profiling of a patient is combined with determination of C4 gene copy number for lupus and/or pre-lupus diagnosis and monitoring.

In an embodiment, a method of identifying lupus or pre-lupus in a patient includes receiving a blood sample for a patient, and performing one or more first cell-bound complement activation product (CB-CAP) assays on the blood sample to generate blood sampling data for the patient. The blood sampling data will include one or more first CB-CAP levels for the patient. The method also includes accessing a control data set that includes control levels for each of the first CB-CAPs. The method includes comparing the first CB-CAP levels for the patient with the control levels to determine whether the first CB-CAPs levels for the patient levels are elevated as compared to the control levels. If the first CB-CAPs levels for the patient levels are elevated as compared to the control levels, then the result may be to determine that the patient has lupus or should be classified exhibiting an increased risk of developing lupus. Otherwise, the method may include accessing a gene copy number data set that includes the number of C4 gene copies in the patient's genome, and determining whether the number of C4 gene copies exceeds a C4 gene copy threshold level. If the number of C4 gene copies equals or exceeds the C4 gene copy threshold level, the result may be determining that the patient neither has lupus nor should be classified as exhibiting an increased risk of developing lupus. If the number of C4 gene copies does not exceed the C4 gene copy threshold level, then the method may include calculating a correction factor determined by the extent of the individual's reduced C4 GCN, multiplying one or more first CB-CAP levels by the correction factor to produce one or more corrected CB-CAP levels, accessing the control data set comprising a control level for each of the CB-CAPs, and comparing the corrected CB-CAP levels for the patient with the control levels to determine whether the corrected CB-CAPs levels for the patient levels are elevated as compared to the control levels. If the corrected CB-CAP levels are elevated as compared to the control levels, then the result may be determining that the patient has lupus or should be classified exhibiting an increased risk of developing lupus. If not, then the result may be determining that the patient does not have lupus and should not be classified as exhibiting an increased risk of generating lupus. The method also may include generating a report of the result, wherein the report includes an indication of whether the patient has lupus or is classified as exhibiting an increased risk of developing lupus.

In an alternate embodiment, a method of identifying lupus or pre-lupus in a patient includes receiving a blood sample for a patient, and performing one or more first cell-bound complement activation product (CB-CAP) assays on the blood sample to generate blood sampling data for the patient. The blood sampling data will include one or more first CB-CAP levels for the patient. The method also includes accessing a control data set that includes control levels for each of the first CB-CAPs. The method includes comparing the first CB-CAP levels for the patient with the control levels to determine whether the first CB-CAPs levels for the patient levels are elevated as compared to the control levels. If the first CB-CAPs levels for the patient levels are elevated as compared to the control levels, then the result may be to determine that the patient has lupus or should be classified exhibiting an increased risk of developing lupus. Otherwise, the method may include accessing a gene copy number data set that includes the number of C4 gene copies in the patient's genome, and determining whether the number of C4 gene copies exceeds a C4 gene copy threshold level. If the number of C4 gene copies equals or exceeds the C4 gene copy threshold level, the result may be determining that the patient neither has lupus nor should be classified as exhibiting an increased risk of developing lupus. If the number of C4 gene copies does not exceed the C4 gene copy threshold level, then the method may include identifying one or more second CB-CAP levels for the patient for one or more second CB-CAPs, and comparing the one or more second CB-CAP levels for the patient with control levels for the one or more second CB-CAPs in the data set to determine whether the one or more second CB-CAP levels are elevated with respect to the control levels for the one or more second CB-CAPs. If the one or more second CB-CAP levels are elevated with respect to the control levels for the one or more CB-CAPs, the result may be determining that the patient has lupus or should be classified as exhibiting an increased risk of developing lupus. Otherwise, the result may be determining that the patient does not have lupus and should not be classified as exhibiting an increased risk of developing lupus. The method may then include generating a report comprising an indication of whether the patient has lupus or is classified as exhibiting an increased risk of developing lupus.

In either of the embodiments listed above, the method may further include the steps of obtaining a sample of genomic DNA from the patient and determining the number of C4 gene copies in the patient's genome for one or both of C4A and C4B in the patient's genome. The number of C4 gene copies for the patient may be the C4A gene copy number, C4B gene copy number or a total of the two gene copy numbers.

In either of the embodiments listed above, the method also may include determining the C4 gene copy threshold level by accessing the control data set, identifying a mean or median gene copy number for a segment of patients in the control data set, and setting the C4 gene copy number as a level equal to one or more standard deviations from the identified mean or median gene copy number.

In either of the embodiments listed above, the first CB-CAP levels may include measurements for T-C4d, B-C4d, E-C4d, and/or other CB-CAPs described in this document.

In either of the embodiments listed above, each instance of determining that the patient has lupus or should be classified as exhibiting an increased risk of developing lupus may include: (i) if the patient meets at least a threshold level of classification criteria, determining that the patient has lupus; and (ii) if the patient does not meet at least the threshold level of classification criteria but meets at least one of the criteria, classifying the patient as exhibiting an increased risk of developing lupus. Optionally, the classification criteria may include any or all of the following: serositis, oral ulcers, arthritis, photosensitivity, blood disorders, renal involvement, antinuclear antibodies, immunologic phenomena, neurologic disorder, malar rash and discoid rash.

In the second embodiment above, optionally the first CB-CAP levels may include measurements for T-C4d and B-C4d, and the one or more second CB-CAP levels may include a measurement for E-C4d. Alternatively, the first CB-CAP levels may include measurements for E-C4d and B-C4d, and the one or more second CB-CAP levels may include a measurement for T-C4d.

The method also may include monitoring disease activity in a patient by performing steps such as those above, and then repeating them with new samples taken from the patient at a later point in time. The new samples will be compared to the control levels, which may be the data set.

Any of the embodiments above may be implemented in whole or in part using a system that includes a data storage facility holding a control data set of blood sampling data for a control subject population, wherein a first group of the subjects in the population are known to have lupus and a second group of the subjects in the population are known to not have lupus, and wherein the blood sampling data includes levels of cell-bound complement activation products (CB-CAPs) for each of the subjects. The system also may include a processing device and a computer-readable medium containing programming instructions that are configured to instruct the processing device to perform any or all of the steps described above for each embodiment.

DETAILED DESCRIPTION

Figure 1:
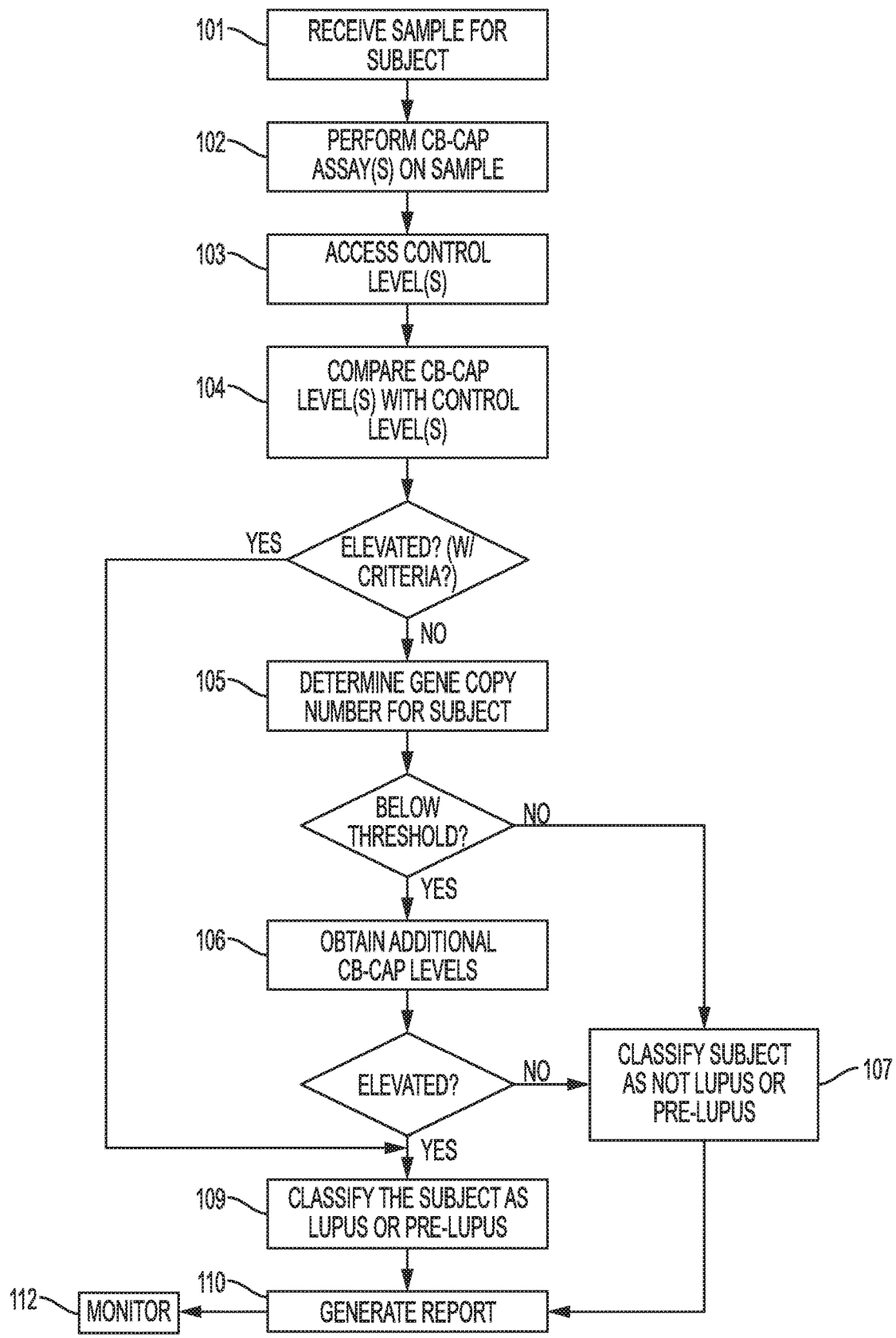
FIG. 1 is a flowchart describing various steps in a data collection and classification process.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

A "cell-bound complement activation product" or "CB-CAP" is a combination of one or more complement activation products and a blood cell (including, but not limited to, an erythrocyte, reticulocyte, T lymphocyte, B lymphocyte, monocyte, granulocyte, eosinophil, basophil or platelet) to which the complement activation product is bound.

As used in this document, a "control" level of any CB-CAP refers, in some embodiments, to a level of that CB-CAP obtained from a sample obtained from one or more individuals who do not suffer from the autoimmune, inflammatory or other disease or disorder that is of interest in the investigation. The level may be measured on an individual-by-individual basis, or on an aggregate basis such as an average. A "control" level can also be determined by analysis of a population of individuals who have the disease or disorder but are not experiencing an acute phase of the disease or disorder. A "control" cell or sample may be used to obtain such a "control" level. A "control" cell or sample may be obtained from one or more individuals who do not suffer from the autoimmune, inflammatory or other disease or disorder that is of interest in the investigation. A "control" cell or sample can also be obtained from a population of individuals who have the disease or disorder but are not experiencing an acute phase of the disease or disorder. In some embodiments, a "control" level of a respective CB-CAP, cell or sample is from the same individual for whom a diagnosis is sought or whose condition is being monitored, but is obtained at a different time. In certain embodiments, a "control" level, sample or cell can refer to a level, sample or cell obtained from the same patient at an earlier time, e.g., weeks, months, or years earlier.

As used in this document, "a difference from a control level" refers to a difference that is statistically significant, as determined by any statistical analysis method now or hereafter used by those in the art. A difference from a control level refers to a statistically significant difference between a control level of a respective CB-CAP and a level of the same CB-CAP from an individual for whom diagnosis or other information is sought, i.e., an experimental level. Those of skill will recognize that many methods are available to determine whether a difference is statistically significant, and the invention is not limited to the particular methods and examples of statistical significance that are described below.

As used herein, "systemic lupus erythematosus", "SLE", or "lupus" is the prototypic autoimmune disease resulting in multiorgan involvement. This anti-self response is characterized by autoantibodies directed against a variety of nuclear and cytoplasmic cellular components. These autoantibodies bind to their respective antigens, forming immune complexes which circulate and eventually deposit in tissues. This immune complex deposition and consequential activation of the complement system causes chronic inflammation and tissue damage.

As used herein, the term "subject" is used to mean an animal, including, without limitation, a mammal. The mammal may be a human. The terms "subject" and "patient" may be used interchangeably.

As used in this document, the term "pre-lupus" refers to a classification or pre-existing condition that may serve as a preliminary indicator that a patient is at increased risk of developing lupus. A patient diagnosed with pre-lupus will have certain characteristics that would correspond to definite lupus, but has not yet developed or been diagnosed with definite lupus.

The pre-lupus condition might be considered an equivalent of a precancerous or premalignant condition, which is a state associated with a significantly increased risk of developing cancer or malignancy that should be treated accordingly. Examples of precancerous or premalignant states include colon polyps, associated with an increased risk of developing colon cancer, Barrett's esophagus, associated with an increased risk of developing esophageal cancer, cervical dysplasia, associated with an increased risk of developing cervical cancer, actinic keratosis, associated with an increased risk of developing skin cancer, and premalignant lesions of the breast, associated with an increased risk of developing breast cancer. In the majority of precancerous states, treatment of the lesion reduces or eliminates the risk of developing cancer. As such, early detection is essential. The pre-lupus condition can be viewed in a similar context. Patients with pre-lupus are at increased risk of developing definite lupus, however they may not. Early detection and appropriate treatment are essential to reducing the risk of disease progression.

Pre-lupus is distinct from and is to be distinguished from "Probable" lupus. A diagnosis of probable lupus is often rendered because the diagnosis of lupus remains an art. There is no blood test or physical manifestation of the disease that can absolutely guarantee an accurate diagnosis of lupus. Therefore, "probable lupus" refers to the likelihood that a patient actually has definite lupus at a given time. This is in contrast to "pre-lupus" which indicates that a patient does not have definite lupus at a given time but rather is at increased risk of eventually developing the disease, although it is possible the patient will never do so.

The following abbreviations may be used in this document:
(1) anti-dsDNA—anti-double stranded DNA
(2) CB-CAPs—cell-bound complement activation products
(3) C4d—complement C4 activation product C4d
(4) GCN—gene copy number
(5) SD—standard deviation
(6) SLE—systemic lupus erythematosus
(7) B-C4d—B cell-bound C4d
(8) E-C4d—Erythrocyte-bound C4d
(9) T-C4d—T cell-bound C4d
(10) P-C4d—Platelet-bound C4d
(11) R-C4d—Reticulocyte-bound C4d
(12) G-C4d—Granulocyte-bound C4d
(13) M-C4d—Monocyte-bound C4d
(14) Eos-C4d—Eosinophil-bound C4d
(15) Baso-C4d—Basophil-bound C4d Lupus continues to pose both diagnostic and management challenges to physicians, in part due to the dearth of reliable tests and biomarkers. The current standard for diagnosing lupus is a rheumatologist's judgment, based primarily on a standard classification scheme developed by the American College of Rheumatology (ACR). The ACR criteria are a set of clinical criteria that a medical professional may use to determine whether a patient has lupus, and include: (1) serositis; (2) oral ulcers; (3) arthritis; (4) photosensitivity; (5) blood disorders; (6) renal involvement; (7) antinuclear antibodies; (8) immunologic phenomena; (9) neurologic disorder; (10) malar rash; and (11) discoid rash. A diagnosis of definite lupus is made when a patient has met at least four of the eleven ACR criteria of clinical symptoms or laboratory tests. Because the various manifestations of lupus may not manifest simultaneously, it often takes years before four criteria are met and a diagnosis is eventually made. Similar criteria have been adopted by the Systemic Lupus International Collaborating Clinics (SLICC).

To circumvent this dilemma, a class of patients who have met fewer than four ACR or SLICC criteria but nonetheless are suspected to have lupus may be given a diagnosis of "pre-lupus." However, it is difficult to identify which patients who met fewer than four of the criteria should continue to be associated with a risk of developing lupus, rather than being considered free from the disease. Some patients with pre-lupus may go on to develop definite lupus, potentially suffering from organ damage that might have occurred unnecessarily due to the missed opportunity of early treatment. Pre-lupus also can be difficult to diagnose, although some methods have recently emerged as described in U.S. Pat. No. 9,495,517. Improving the timeliness and accuracy of diagnosis of lupus would be greatly facilitated by the availability of biomarkers in addition to CB-CAPs that can help identify patients who have "pre-lupus" and will benefit from early management of preventable organ damage.

In certain embodiments described in this document, a patient who is determined to meet at least one but fewer than four classification criteria for lupus may be considered for a diagnosis of pre-lupus. In some embodiments, these classification criteria may be, but are not limited to, those published by the ACR and/or SLICC.

Numerous studies have indicated a prominent role of the complement system in the pathogenesis of lupus. Because complement proteins are abundantly present in the circulation and can readily interact with circulating cells, the inventors have determined that complement activation products bound to circulating cells may serve as more informative lupus and pre-lupus biomarkers than soluble complement proteins. Indeed, significant levels of complement C4-derived activation products, particularly C4d, are present specifically on the surfaces of erythrocytes, reticulocytes, platelets, and lymphocytes of patients with lupus and pre-lupus. These CB-CAPs can serve as unique biomarkers not only for diagnosis but also for monitoring disease activity in patients with lupus and pre-lupus.

Human complement C4 protein is known to be the product of two isotypic genes, C4A and C4B. Due to duplications/deletions of the chromosome segment housing the C4 gene loci, some individuals may have more than two or fewer than two copies of the C4A and C4B genes. Consequently, a given individual may have as few as none or as many as up to nine copies of the C4 genes in total. The copy number of C4A can range from 0 to 6, and the copy number of C4B can range from 0 to 4. Such variations in the C4 gene copy number (GCN) can potentially lead to variations in C4 protein production, resulting in or not a correlation between C4 GCN and serum C4 levels. The present inventors have demonstrated that significant levels of C4d, an activation product of C4, are specifically present on the surface of circulating blood cells in patients with systemic lupus erythematosus (SLE; lupus) and pre-lupus. These so-named "cell-bound complement activation products (CB-CAPs)" can be valuable diagnostic, monitoring and prognostic (stratification) biomarkers for SLE and pre-lupus.

Given that C4 protein levels (and hence C4d levels) may not only be influenced by the disease status but also by the C4 GCN, while not intending to be bound by theory, the inventors have found that low C4 GCN may lead to persistently low CB-CAP levels in some SLE patients and therefore reduce the diagnostic utility (sensitivity/specificity) of CB-CAP biomarkers in these patients. Thus, the inventors describe in this document methods that include determination of C4 genotype along with CB-CAP signatures to provide a more informative determination of lupus and pre-lupus diagnosis and monitoring.

In certain embodiments described in this document, a patient's gene copy numbers for C4A, C4B, or both C4A and C4B may be used.

In embodiments described in this document, CB-CAPs may be assayed for one or more of a number of cell types, including, but not limited to, C4d associated with erythrocytes (E-C4d), reticulocytes (R-C4d), T lymphocytes (T-C4d), B lymphocytes (B-C4d), monocytes (M-C4d), granulocytes (G-C4d), platelets (P-C4d), eosinophils (Eos-C4d), and/or basophils (Baso-C4d).

In embodiments described in this document, CB-CAP levels may be determined by any suitable method. Such assays for CB-CAPs may include, but are not limited to, enzyme-linked immunoassays and use of polyclonal antibodies. In embodiments, monoclonal antibodies may be used. A flow cytometer or other suitable device may be used to determine the CB-CAP levels.

The determinations described in this document, such as, for example, diagnosing or monitoring lupus or pre-lupus in an individual, can be carried out manually or may be carried out using an automated system and/or equipment, in which a blood sample is analyzed automatically to make the necessary determination or determinations, and the comparison with the base or reference value is carried out automatically, using computer software appropriate to that purpose.

Referring to FIG. 1, in an embodiment a blood sample is received for a subject patient (step 101). One or more CB-CAP assays are performed on the patient (step 102) to generate blood sampling data for the patient. The blood sampling data will include one or more CB-CAP levels for the patient. In embodiments, CB-CAPs may be assayed for one or more of a number of cell types, including, but not limited to, C4d associated with: erythrocytes (E-C4d), reticulocytes (R-C4d), T lymphocytes (T-C4d), B lymphocytes (B-C4d), monocytes (M-C4d), granulocytes (G-C4d), platelets (P-C4d), eosinophils (Eos-C4d), and/or basophils (Baso-C4d). In certain embodiments, the CB-CAP levels determined may be those of any combination of these or other CB-CAPs as components of a CB-CAP panel with CB-CAPs such as those described above. In certain embodiments, CB-CAP levels may comprise measurements for one or more of T-C4d, B-C4d, or E-C4d.

The method may then include accessing a control data set containing a set of CB-CAP control levels, and extracting from the data set control levels for each of the CB-CAPs for which assays are performed (step 103). The control levels may be stored in a data storage facility holding a control data set of blood sampling data for a subject population. Some groups of the subject population may be known to have lupus or pre-lupus, while others may be known to not have lupus or pre-lupus. The blood sampling data will include levels of one or more CB-CAPs for each of the subjects.

In embodiments, the control data set may include measurements of control levels for various CB-CAPs, including, but not limited to, C4d associated with erythrocytes (E-C4d), reticulocytes (R-C4d), T lymphocytes (T-C4d), B lymphocytes (B-C4d), monocytes (M-C4d), granulocytes (G-C4d), platelets (P-C4d), eosinophils (Eos-C4d), and/or basophils (Baso-C4d).

The method may then include comparing the patient's CB-CAP levels with the control levels to determine whether the patient's levels are elevated as compared to the control levels (step 104). When a blood sample is taken from a patient for whom a diagnosis is desired, the sample may be analyzed for the levels of any or all of the CB-CAPs for which levels are also available in the data set. In embodiments, the sampling data may be entered into or received by a processing device, which will compare the CB-CAP levels from the patient's sample with the CB-CAP levels in the data set to determine a number and/or levels of CB-CAPs for which the patient exhibits an elevated level. A level of a CB-CAP in the patient's sample may be determined as "elevated" if it exhibits a statistically significant difference from (above) a control level of the same CB-CAP in the control set. As an example, if the level of the CB-CAP in the patient's sample is at least one, two or more standard deviations above the mean or median level of the same CB-CAP in the control set, the level may be considered to be elevated. Other methods of determining statistical significance may be used to determine whether a level is elevated.

In some embodiments, this analysis may focus on determining whether one or two particular CB-CAP levels are elevated. For example, the analysis may assess whether the subject's T-C4d and B-C4d levels are elevated with respect to the baseline. In embodiments, if the levels are elevated, the method may include classifying the patent as having either pre-lupus or lupus 109. For example, if the CB-CAP levels are elevated and one or more other conditions are satisfied (such as but not limited to: the patient exhibited four or more American College of Rheumatology or SLICC classification criteria for lupus), the method may include classifying the patient as having lupus. If the levels are elevated but other criteria are not satisfied (such as but not limited to: the patient does not exhibit four or more American College of Rheumatology or SLICC classification criteria for lupus), the method may include classifying the patient as not having lupus but exhibiting an elevated risk for developing lupus (a condition that may be referred to as "pre-lupus") (step 109).

If the patient's CB-CAP levels are not elevated or are elevated but not considered to be high enough to be in the range that is determined to be diagnostic of lupus or pre-lupus, then the method also may include determining a C4 gene copy number for the subject (step 105). The gene copy set comprises a number of C4A and/or C4B gene copies in the patient's genome. As with the control level data set, the gene copy number data set may be stored in a data storage facility. Alternatively, in embodiments, the gene copy number data set may be generated by identifying the number of C4 gene copies by extracting the numbers from the patient's genome. In some embodiments, the method may include the steps of determining the gene copy number by obtaining a sample of genomic DNA from the patient, and determining gene copy numbers for C4A and/or C4B in the patient's genome.

In various embodiments described in this document, C4 gene copy-number (GCN) or C4 copy number variation (CNV) determinations may be performed by any suitable method. In certain embodiments, one or more of the following may be employed: TaqI genomic Southern blots may be performed to determine the copy-numbers of (a) long C4 genes linked to RP1 or RP2, short C4 genes linked to RP1 or RP2, (b) CYP21B and CYP21A, and (c) TNXB and TNXA. Through TaqI genomic RFLP, the copy-numbers of total C4, C4L, C4S, and the RCCX modular structures may be elucidated. PshAI-PvuII RFLP Southern blots and/or qPCR assays may be performed to determine the copy-numbers of C4A and C4B. Long-range mapping experiments employing PmeI digested genomic DNA resolved by pulsed field gel electrophoresis and processed by Southern blot analyses may also be performed to further validate the RCCX haplotypes. In embodiments, additional methods may include whole exome sequencing, whole genome sequencing, sequencing of the entire C4 loci or other next generation sequencing approaches.

If the number of C4A gene copies, C4B gene copies or both is at or above a threshold, then the method may include using this to confirm that the patient should not be classified as pre-lupus or lupus (step 107). On the other hand, if the C4 gene copy number(s) is below the threshold, then the method may include at least two options. First, in embodiments, the subject could be classified as lupus or pre-lupus by reviewing one or more additional CB-CAP levels for the subject (step 106) to determine whether the additional CB-CAP levels exceed a threshold, and if so classifying the patient as lupus or pre-lupus, otherwise confirming that the patient should not be so classified. For example, in embodiments, if the CB-CAP levels reviewed in step 104 are T-C4d and B-C4d, the method may include assessing the patient's E-C4d CB-CAP level in step 106. Similarly, in embodiments, if the CB-CAP levels reviewed in step 104 are E-C4d and B-C4d, the method may include assessing the patient's T-C4d CB-CAP level in step 106. Other combinations of CB-CAP measurements may be used. In embodiments, CB-CAPs may be assayed for one or more of a number of cell types, including, but not limited to, C4d associated with: erythrocytes (E-C4d), reticulocytes (R-C4d), T lymphocytes (T-C4d), B lymphocytes (B-C4d), monocytes (M-C4d), granulocytes (G-C4d), platelets (P-C4d), eosinophils (Eos-C4d), and/or basophils (Baso-C4d).

Second, in embodiments, a CB-CAP level that is below a certain threshold may be multiplied by a correction factor determined by the extent of the individual's reduced C4 GCN. Thus, in some embodiments in which CB-CAP levels are elevated but not considered to be in a range diagnostic of lupus or pre-lupus, such "false negatives" may be corrected by a multiplication factor to compensate for the reduced C4 GCN. See, for example, FIG. 2.

The threshold level for the C4 gene copy number(s) may be any suitable number, such as 1, 2, 3 or another number. Optionally, the threshold level for the C4 gene copy number(s) can be determined from the gene copy number data set described above. For example, the threshold level may be a number that is one, two, three, or another number of standard deviations below the mean (or median) level for all patients in the data set, or for all patients in the data set who are known to not have lupus or pre-lupus.

If the one or more additional CB-CAP levels exceed the threshold, then the method may include classifying the patient as lupus or pre-lupus (step 109), otherwise the method may include classifying the patient as not lupus or pre-lupus (step 107). In certain embodiments, the determination of whether the patient should be classified as lupus or pre-lupus at this point may depend on whether the patient exhibits at least four (or another threshold number of) classification criteria such as those described above. In embodiments, if the patient meets more than the threshold number of classification criteria, the method may include classifying the patient as exhibiting lupus. If not, the method may include classifying the patient as pre-lupus.

As noted above, the method described above may be used to not only to determine whether to classify a patient as exhibiting lupus, but also to determine whether to classify a patient as exhibiting a risk of developing lupus (i.e., being pre-lupus).

The methods described above also may be used to monitor SLE disease activity of a patient who has lupus or exhibits an increased risk of developing lupus (pre-lupus). This may be done by repeating the sampling and comparing as described above at periodic intervals to determine whether the patient's CB-CAP levels remain stable or increase over time.

At any point in the process, the system may generate a report (step 110) containing the classification of the subject, the determined CB-CAP levels for the subject, and/or the C4 gene copy numbers for the subject. In embodiments, the system may generate a report with a diagnosis, such as the probability level itself, or one or more narrative or graphic indicia that describes the reasons why the patient is considered to exhibit (or not exhibit) lupus or pre-lupus. In embodiments, the report may provide an assessment of whether the patient could be classified as a pre-lupus patient. In embodiments, the report may provide an assessment of whether the patient could be classified as a lupus patient. The system may be remote from that of a patient or medical professional, and some or all of the elements of the system may be present in multiple systems, such as a cloud-based system where the control data set is remote from the system that performs the processing and analysis, but connected via one or more communication networks.

In embodiments, methods are provided for monitoring (step 112) the level of lupus disease activity in a patient. In this case, the process may be repeated by obtaining a new sample (step 101) from the patient to monitor disease activity. The newly assayed CB-CAP levels (step 102) are compared to control levels (step 103), while may be the control levels from the data set or the measured levels of a sample obtained from the same patient at an earlier time. If the new levels are determined to be elevated with respect to the control levels (step 109), the patient may be classified as exhibiting an increased level of systemic lupus erythematosus disease activity.

Figure 2:
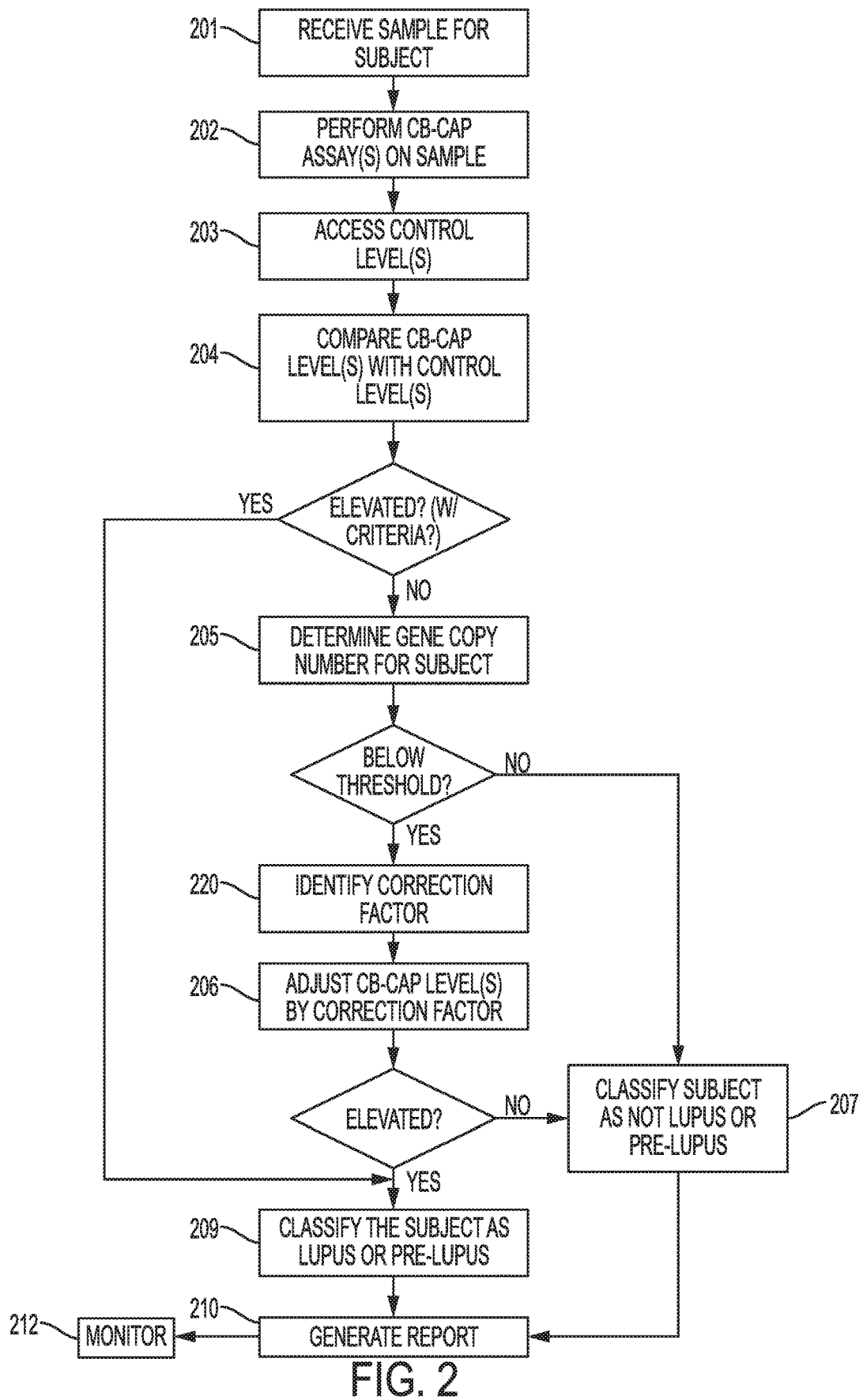
FIG. 2 is a flowchart describing various steps in an alternate data collection and classification process.

Referring to FIG. 2, in an alternate embodiment a blood sample is received for a subject patient (step 201). One or more CB-CAP assays are performed on the patient (step 202) to generate blood sampling data for the patient. The blood sampling data will include one or more CB-CAP levels for the patient. In embodiments, CB-CAPs may be assayed for one or more of a number of cell types, including, but not limited to, C4d associated with; erythrocytes (E-C4d), reticulocytes (R-C4d), T lymphocytes (T-C4d), B lymphocytes (B-C4d), monocytes (M-C4d), granulocytes (G-C4d), platelets (P-C4d), eosinophils (Eos-C4d), and/or basophils (Baso-C4d). In certain embodiments, the CB-CAP levels determined may be those of any combination of these and other CB-CAPs as components of a CB-CAP panel. In certain embodiments, the CB-CAP levels may comprise measurements for one or more of T-C4d, B-C4d, and E-C4d.

The method may then include accessing a control data set containing a set of CB-CAP control levels, and extracting from the data set control levels for each of the CB-CAPs for which assays are performed (step 203). The control levels may be stored in a data storage facility holding a control data set of blood sampling data for a subject population. Some groups of the subject population may be known to have lupus or pre-lupus, while others may be known to not have lupus or pre-lupus. The blood sampling data will include levels of one or more CB-CAPs for each of the subjects. In embodiments, the control data set may include measurements of control levels for various CB-CAPs, including, but not limited to, C4d associated with erythrocytes (E-C4d), reticulocytes (R-C4d), T lymphocytes (T-C4d), B lymphocytes (B-C4d), monocytes (M-C4d), granulocytes (G-C4d), platelets (P-C4d), eosinophils (Eos-C4d), and/or basophils (Baso-C4d).

The method may then include comparing the CB-CAP levels with the control levels to determine whether the patient's levels are elevated as compared to the control levels (step 204). When a blood sample is taken from a patient for whom a diagnosis is desired, the sample may be analyzed for the levels of any or all of the CB-CAPs for which levels are also available in the data set.

If the patient's CB-CAP levels are not elevated and/or the other criteria are not satisfied, then the method also may include determining a C4 gene copy number for the subject (step 205). The gene copy set comprises a number of C4A and/or C4B gene copies in the patient's genome. As with the control level data set, the gene copy number data set may be stored in a data storage facility. Alternatively, the gene copy number data set may be generated by identifying the number of C4 gene copies by extracting the numbers from the patient's genome. In some embodiments, the method may include the steps of determining the gene copy number by obtaining a sample of genomic DNA from the patient, and determining gene copy numbers for C4A and/or C4B in the patient's genome.

If the number of C4A gene copies, C4B gene copies or both is at or above a threshold, then the method may include using this to confirm that the patient should not be classified as pre-lupus or exhibiting lupus (step 207). On the other hand, if the C4 gene copy number(s) is below the threshold, the C4 gene copy number may be used to identify a correction factor determined by the extent of the individual's reduced C4 GCN (step 220). A CB-CAP level that is below a certain threshold may be multiplied by such a correction factor (step 206). And the corrected CB-CAP levels may then be compared to the control levels.

If one or more of the corrected CB-CAP levels are determined to be elevated as compared to control levels, then the method may include classifying the patient as lupus or pre-lupus (step 209), otherwise the method may include classifying the patient as not exhibiting lupus or pre-lupus (step 207). As discussed elsewhere in this document, in embodiments, the determination of whether the patient should be classified as lupus or pre-lupus at this point may depend on whether the patient exhibits at least four (or another threshold number of) classification criteria such as those described above. If the patient meets more than the threshold number of classification criteria, the method may include classifying the patient as exhibiting lupus. If not, the method may include classifying the patient as pre-lupus.

At any point in the process, the system may generate a report (step 210) containing the classification of the subject, the determined CB-CAP levels for the subject, and/or the C4 gene copy numbers for the subject. In embodiments, the system may generate a report with a diagnosis, such as the probability level itself, or one or more narrative or graphic indicia that describes the reasons why the patient is considered to exhibit (or not exhibit) lupus or pre-lupus. In embodiments, the report may provide an assessment of whether the patient could be classified as a pre-lupus patient. In embodiments, the report may provide an assessment of whether the patient could be classified as a lupus patient. The system may be remote from that of a patient or medical professional, and some or all of the elements of the system may be present in multiple systems, such as a cloud-based system where the control data set is remote from the system that performs the processing and analysis, but connected via one or more communication networks.

In embodiments, methods are provided for monitoring (step 212) the level of lupus disease activity in a patient. A new sample may be obtained (step 201) from the patient to monitor disease activity. The new assayed CB-CAP levels (step 202) are compared to control levels (step 203), which may be the control data set levels or measured levels from a sample obtained from the same patient at an earlier time. If the new levels are determined to be elevated with respect to the control levels (step 209), the patient may be classified as exhibiting an increased level of systemic lupus erythematosus disease activity.

In embodiments, methods and systems are provided in which various aspects of the methods and systems described above and depicted in FIGS. 1 and 2 may be combined. In an embodiment, if a patient's CB-CAP level(s) on one or more cell types is considered to be less than that resulting in a classification as lupus or pre-lupus, the C4 GCN of the patient is determined. If that C4 GCN is less than a certain threshold (e.g. <4), then CB-CAPs on cell types other than those initially measured could be determined subsequently. For example, if BC4d and TC4d were measured initially and determined to be normal or less than that required to diagnose lupus or pre-lupus and C4 GCN were determined to be <4, then additional CB-CAP levels could be determined on cells such as erythrocytes (EC4d) and/or platelets (PC4d). Alternatively, if a patient's CB-CAP level(s) on one or more cell types is considered to be less than that resulting in classification as lupus or pre-lupus, and the C4 GCN of the patient is determined to be less than a certain threshold (e.g. <4), then the embodiment described in FIG. 2 may be used. In this embodiment, the CB-CAP levels which are measured and determined to be less than that required to diagnose lupus or pre-lupus, are adjusted by a correction factor intended to compensate for the patient's C4 genetic deficiency. These two embodiments are not mutually exclusive. The methods displayed in FIGS. 1 and 2 could be used together to further analyze a patient sample found to have: (a) CB-CAP levels below a lupus/pre-lupus diagnostic cutoff; and (b) C4 GCN below a certain threshold. Additional CB-CAP levels could be determined on the sample, and a correction factor could also be used to adjust the levels of the CB-CAP levels determined on the original cell types. For example, if TC4d and BC4d were determined to be non-diagnostic of lupus and/or pre-lupus and the C4 GCN was found to be below a certain threshold e.g., <4, then EC4d, PC4d and/or other CB-CAPs could be determined AND the TC4d and/or BC4d levels could be adjusted with a correction factor to compensate for the patient's genetic deficiency. The results could be further analyzed in an algorithm to classify the patient as lupus or pre-lupus.

Example 1

The present inventors conducted a cross-sectional analysis of 195 SLE patients. Genomic DNA samples were prepared from buffy coats of peripheral blood and used for genotyping experiments. The C4 isotypes and GCNs were determined by Southern blot analysis using DNA obtained from respective SLE patients. (Yang, Y. et al. Gene copy-number variation and associated polymorphisms of complement component C4 in human systemic lupus erythematosus (sle): Low copy number is a risk factor for and high copy number is a protective factor against sle susceptibility in european americans. *American Journal of Human Genetics* 2007, 80, 1037-1054; Wu, Y. L, et al. Phenotypes, genotypes and disease susceptibility associated with gene copy number variations: Complement C4 CNVs in European American healthy subjects and those with systemic lupus erythematosus. *Cytogenetic and Genome Research* 2008, 123, 131-141.) CB-CAP levels on peripheral blood cells of the same patients were measured by flow cytometry. (Manzi, S., et al., Measurement of erythrocyte C4d and complement receptor 1 in systemic lupus erythematosus. *Arthritis Rheum* 2004, 50, 3596-3604; Liu, C. C. et al., Lymphocyte-bound complement activation products as biomarkers for diagnosis of systemic lupus erythematosus. *Clin Transl Sci* 2009, 2, 300-308; Liu, C. C., et al., Reticulocytes bearing c4d as biomarkers of disease activity for systemic lupus erythematosus. *Arthritis Rheum* 2005, 52, 3087-3099; Navratil, J. S, et al. Platelet c4d is highly specific for systemic lupus erythematosus. *Arthritis Rheum* 2006, 54, 670-674).

The patients were categorized based on the numbers of copies of either or both of the C4A and C4B genes. The CB-CAP levels were determined and correlated with the C4A/C4B GCN. CB-CAP levels were analyzed either as continuous data (specific mean fluorescence levels) or categorical data (positive or negative; positive defined as CB-CAP level higher than the mean+2 SD of a healthy control cohort). Continuous data were analyzed using Kruskal-Wallis test and post hoc pairwise comparison as well as linear regression analysis. Categorical variables were analyzed using Fisher's exact test or chi-square test. All statistical analyses were performed using the STATA/SE version 11.0 for Windows (Stata Corporation, College Station, TX) and SAS V9.3 (SAS Institute, Cary, NC).

Example 2

As shown in Table 1 and Table 2, the results demonstrate that CB-CAP levels, particularly those of T cell-bound C4d (T-C4d) and B cell-bound C4d (B-C4d), were associated with increasing numbers of the copies of C4 genes. Specifically, T-C4d and B-C4d levels correlated with the C4A GCN but not with the C4B GCN (Table 3; data shown only for C4A genes). Remarkably, 100% of patients with no C4A genes (C4A GCN=0; homozygous C4A deficiency) had low levels of CB-CAPs on T cells and B cells. With the presence of even one copy of the C4A gene, the CB-CAP levels were elevated significantly (Table 4). While not intending to be bound by any theory, this latter finding suggests that the C4A gene may play an important role in generating C4d that is capable of binding to T and B cells.

Figure 3:
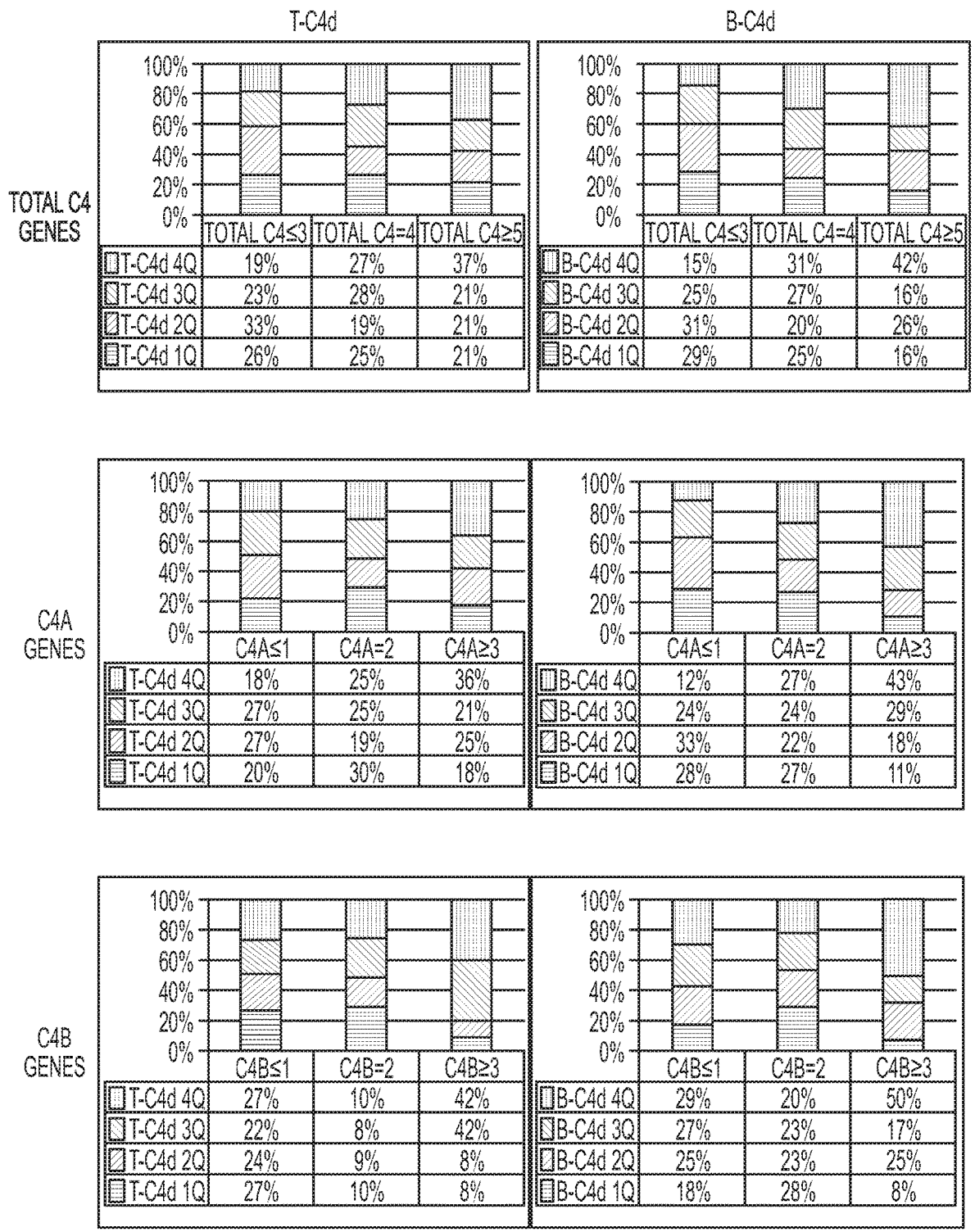
FIG. 3 presents tables showing example analyses performed using the methods described in this document, and it illustrates a correlation between C4 gene copy numbers and T-C4d and B-C4d levels.

Referring to FIG. 3, in an example application, SLE patients were divided into quartiles based on either T-C4d levels or B-C4d levels. The copy numbers of total C4 genes (C4A and C4B), C4A genes, and C4B genes of individual patients were determined as described above. The distribution of patients with different C4 GCNs in the T-C4d/B-C4d quartile scales was plotted and a trend toward a positive correlation between total C4 GCN and C4A GCN and T-C4d/B-C4d level was noticed. Fisher's exact test or Chi-square test was performed to determine the statistical significance of this trend. The p values for the correlation between T-C4d and total C4 GCN, T-C4d and C4A GCN, and T-C4d and C4B GCN, were 0.37, 0.18, and 0.40, respectively. The p values for the correlation between B-C4d and total C4 GCN, B-C4d and C4A GCN, and B-C4d and C4B GCN, were 0.09, 0.044, and 0.27 respectively.

In the example of FIG. 3, when patients were classified into quartiles based on T-C4d and B-C4d levels, it was noted that an increased percentage of patients with more than four copies of the C4 genes were in the highest quartile compared with patients with fewer copies of the C4 genes. Again, this correlation related to the C4A gene, i.e., patients with increasing numbers of C4A gene were more likely in the highest quartile of either T-C4d or B-C4d. Correlation between C4A GCN and B-C4d was statistically significant (p=0.044).

Figure 4:
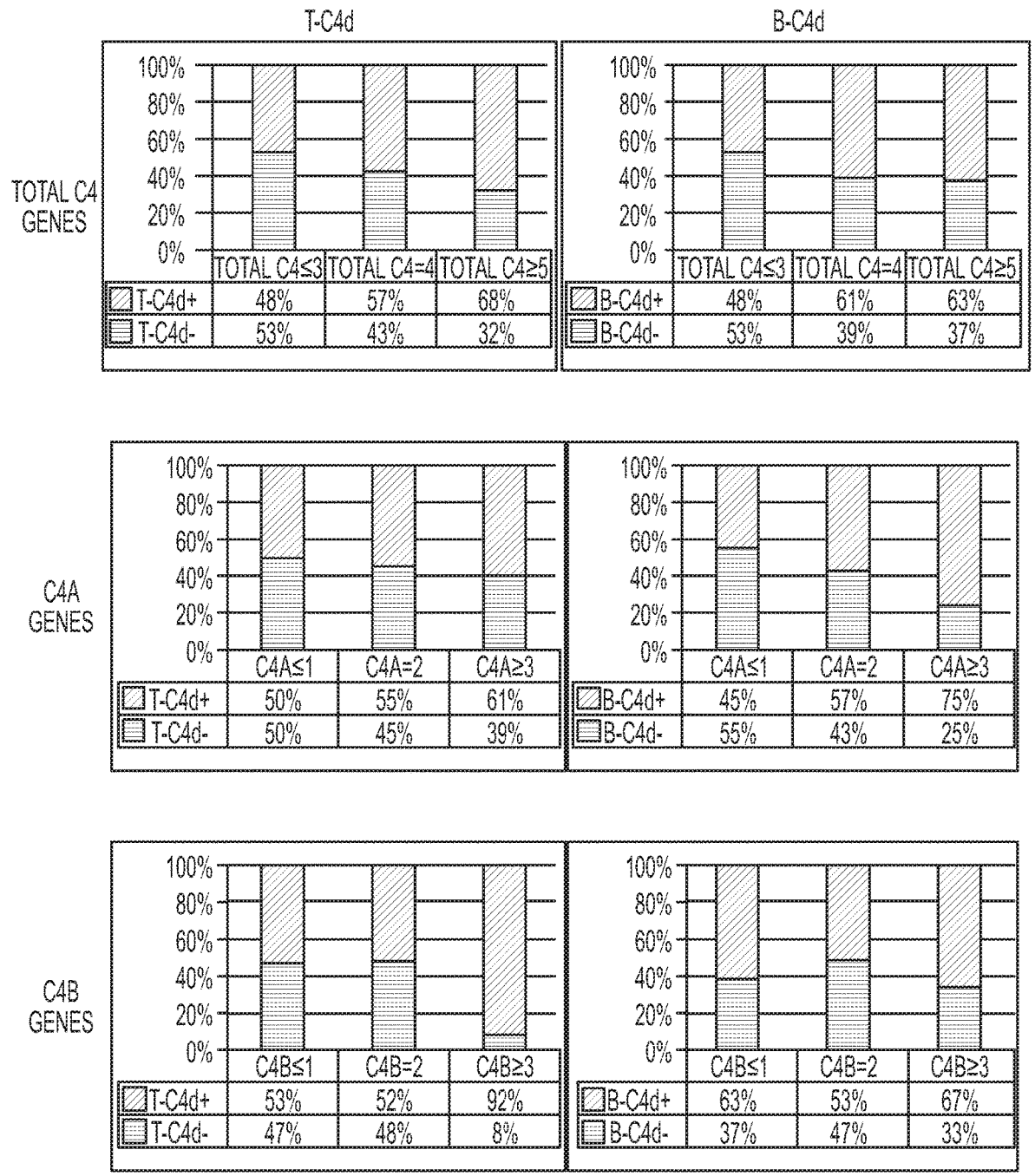
FIG. 4 presents tables that illustrate a correlation between C4 gene copy numbers and T-C4d and B-C4d positivity.

FIG. 4 illustrates an example in which SLE patients were divided into binary groups based on T-C4d or B-C4d positivity. The copy numbers of total C4 genes (C4A and C4B), C4A genes, and C4B genes of individual patients were determined as described above. The distribution of patients with different C4 GCNs in the T-C4d/B-C4d positive and negative group was plotted, and a positive correlation between total C4 GCN and C4A GCN and T-C4d/B-C4d positivity was identified. Fisher's exact test or Chi-square test was performed to determine the statistical significance of this trend. The p values for the correlation between T-C4d positivity and total C4 GCN, T-C4d and C4A GCN, and T-C4d and C4B GCN, were 0.18, 0.64, and 0.028, respectively. The p values for the correlation between B-C4d and total C4 GCN, B-C4d and C4A GCN, and B-C4d and C4B GCN, were 0.15, 0.029, and 0.34 respectively. Thus, when patients were classified into binary groups based on T-C4d or B-C4d positivity, statistically significant correlations were found not only between increasing C4A GCN and B-C4d positivity (p=0.029), but also between increasing C4B GCN and T-C4d positivity (p=0.028) (FIG. 4).

Together, these results indicate a positive correlation of CB-CAP levels, particularly T-C4d and B-C4d, with the C4 GCN in a given SLE patient. While not intending to be bound by any theory, given the complexity of C4 genotypes (isotypic C4A/C4B genes in various copy numbers) and phenotypes (large number of C4A and C4B protein allotypes), the role(s) of C4 in CB-CAPs may involve not only C4 GCN but also protein allotypes expressed in individual patients. The findings described in this document indicate that the utility of CB-CAPs for SLE or pre-lupus diagnosis, monitoring and/or prognosis (stratification) may be enhanced by simultaneous determination of the C4 GCN of individual patients in a personalized manner.

Furthermore, determination of the specific sequences of the C4 genes in a given patient may provide additional guidance for interpreting the results of CB-CAP assay values in that same patient. Together, C4 GCN+CB-CAP assay values, particularly those for TC4d and BC4d but likely others, may be used to generate a score that may guide further laboratory testing and clinical intervention. More specifically, diagnostic, monitoring, prognostic, personalized and/or other tests that are based upon CB-CAP determinations may be interpreted with simultaneous determination of C4 GCN in that individual. Thus, in certain aspects, the present document provides improved methods to stratify patients with lupus or pre-lupus and to personalize their clinical care.

TABLE 1

Correlation between CB-CAP Levels and Total C4 Gene Copy Number*

| Total C4 Gene Copy Number (no of patients) | T-C4d mean ± SD (median; IQR) | B-C4d mean ± SD (median; IQR) |
|---|---|---|
| 2 (n = 10) | 4.9 ± 7.4 (2.5; 0.9-5.7) | 19.1 ± 16.5 (16.5; 9.2-22.2) |
| 3 (n = 66) | 13.2 ± 20.4 (5.0; 2.1-9.6) | 42.3 ± 42.7 (29.1; 11.2-53.5) |
| 4 (n = 99) | 17.0 ± 28.1 (4.2; 1.6-19.5) | 58.0 ± 62.8 (37.4; 10.5-77.9) |
| ≥5 (n = 20) | 29.7 ± 43.9 (11.4; 2.7-36.5) | 100.9 ± 141.5 (33.1; 17.8-93.2) |
| | Overall: p = 0.127 | Overall: p = 0.070 5 vs 2: p = 0.057 |

*Kruskal-Wallis Test and post hoc pairwise comparisons

TABLE 2

Correlation between CB-CAP Levels and Total C4 Gene Copy Number*

| Total C4 Gene Copy Number | T-C4d Estimate (S.E.) P value | B-C4d Estimate (S.E.) P value |
|---|---|---|
| 2** | 0 | 0 |
| 3 | 0.513 (0.314) 0.1720 | 0.296 (0.279) 0.2902 |
| 4 | 0.545 (0.366) 0.1371 | 0.507 (0.272) 0.0633 |
| ≥5 | 1.076 (0.452) 0.018 | 0.827 (0.339) 0.0155 |

*Generalized linear regression analysis
**Reference group

TABLE 3

Correlation between CB-CAP Levels and C4A Gene Copy Number*

| C4A Gene Copy Number | T-C4d Estimate (S.E.) P value | B-C4d Estimate (S.E.) P value |
|---|---|---|
| 0** | 0 | 0 |
| 1 | 1.228 (0.699) 0.0807 | 0.896 (0.543) 0.1009 |
| 2 | 1.058 (0.679) 0.1208 | 1.038 (0.528) 0.0508 |
| 3 | 1.511 (0.736) 0.0414 | 1.440 (0.572) 0.0127 |
| 4 | 1.881 (0.899) 0.0378 | 1.809 (0.699) 0.0104 |

*Generalized linear regression analysis
**Reference group

TABLE 4

Comparison between CB-CAP Levels and Total C4 Gene Copy Number

| C4A Gene Copy number | T-C4d mean ± SD (median; IQR) | B-C4d mean ± SD (median; IQR) |
|---|---|---|
| 0 (n = 5) | 2.2 ± 1.6 (1.9; 1.0-2.6) | 10.6 ± 3.5 (10.1; 8.2-10.9) |
| 1 (n = 49) | 12.8 ± 18.2 (6.0; 2.3-10.5) | 39.6 ± 43.8 (25.1; 13.6-50.8) |
| 2 (n = 113) | 15.5 ± 26.5 (3.5; 1.5-17.5) | 59.3 ± 81.4 (31.4; 10.0-77.9) |
| 3 (n = 23) | 20.8 ± 27.4 (9.2; 3.1-24.9) | 64.7 ± 49.2 (48.8; 28.7-89.8) |
| 4 (n = 5) | 51.0 ± 75.0 (7.0; 0.7-73.7) | 85.9 ± 73.8 (54.7; 27.7-145.8) |

As an example, data such as that shown in Table 4 may be used to determine the correction factor to be applied to each patient's CB-CAP levels. In some embodiments, the correction factor for each GCN and corresponding CB-CAP and may be a multiplier equal to the ratio of the mean for a normal GCN (e.g., 4) to the GCN of the patient. Optionally, the multiplier may be rounded to a particular significant digit or whole number. For example, in Table 4 above, the T-C4d correction factor for a patient with a GCN=1 will be 51.0/12.8=3.98 (which may be rounded to 4), and the B-C4d correction factor for a patient with a GCN=3 may be 85.9/64.7=1.33. Other methods of determining the correction factor are possible. For example, as shown above the correction factor for each GCN/CB-CAP combination may vary based on the control data set used, or it may be a standard correction factor used for all patients regardless of control data set.

Example 3

Table 5 demonstrates the concept of a CB-CAP signature, including the results of C4 GCN determination and levels of positive for PC4d. These data indicate that patients with <4 C4 GCN are likely to be negative/normal for TC4d, BC4d or both and may yield a false negative CB-CAP assay determination for a diagnosis of lupus. However, in some of these individuals other CB-CAP assays such as but not limited to EC4d, RC4d, PC4d, and MC4d may be positive and useful for the diagnosis of lupus or pre-lupus.

TABLE 5

C4 Gene Copy Number (C4 GCN) and CB-CAP Signature in Representative Patients

| Patient ID | Total C4 GCN | C4A GCN | C4B GCN | E-C4d (SMFI) | P-C4d (SMFI) | R-C4d (SMFI) | T-C4d (SMFI) | B-C4d (SMFI) | M-C4d (SMFI) | G-C4d (SMFI) |
|---|---|---|---|---|---|---|---|---|---|---|
| 29624 | 5 | 2 | 3 | 10.67 | 1.22 | 2.49 | 41.10 | 87.07 | 22.46 | 2.40 |
| 103343 | 5 | 4 | 1 | 16.64 | 4.35 | 4.32 | 173.39 | 190.51 | 22.35 | 1.83 |
| 133518 | 5 | 2 | 3 | 16.46 | 10.64 | 11.24 | 62.90 | 193.55 | 23.49 | 6.69 |
| 88795 | 4 | 2 | 2 | 83.63 | 11.60 | 22.64 | 51.83 | 75.91 | 31.31 | 1.94 |
| 98266 | 4 | 2 | 2 | 14.66 | 0.62 | 20.91 | 30.52 | 64.43 | 22.63 | 5.87 |
| 101592 | 4 | 2 | 2 | 13.58 | 5.31 | 8.67 | 49.34 | 102.56 | 14.77 | 4.80 |
| 101601 | 4 | 2 | 2 | 11.44 | 1.20 | 2.04 | 71.75 | 108.97 | 7.93 | 1.76 |
| 101606 | 4 | 2 | 2 | 37.14 | 12.51 | 19.59 | 18.29 | 79.89 | 14.25 | 2.43 |
| 101608 | 4 | 2 | 2 | 26.81 | 1.04 | 30.44 | 16.11 | 130.03 | 10.87 | 2.55 |
| 101680 | 4 | 2 | 2 | 6.14 | 1.66 | 2.33 | 38.12 | 175.08 | 3.48 | 0.34 |
| 103252 | 4 | 4 | 0 | 20.18 | 0.90 | 1.59 | 6.17 | 67.54 | 2.02 | 0.19 |
| 1682 | 3 | 2 | 1 | 18.87 | 26.55 | 8.49 | 165.57 | 164.12 | 36.54 | 10.05 |
| 1715 | 3 | 2 | 1 | 11.11 | 0.24 | 7.73 | 6.89 | 12.26 | 2.12 | 0.63 |
| 18905 | 3 | 1 | 2 | 4.78 | 0.26 | 0.88 | 2.13 | 14.82 | 1.83 | 0.41 |
| 32958 | 3 | 1 | 2 | 15.52 | 1.83 | 1.96 | 3.34 | 19.65 | 11.52 | 2.65 |
| 91251 | 3 | 2 | 1 | 9.41 | 2.82 | 1.24 | 3.67 | 36.75 | 3.54 | 2.22 |
| 97387 | 3 | 1 | 2 | 8.94 | 1.40 | 4.71 | 2.50 | 11.48 | 6.01 | 2.13 |
| 101693 | 3 | 1 | 2 | 11.06 | 24.10 | 4.12 | 47.96 | 185.80 | 54.21 | 7.13 |
| 147814 | 3 | 2 | 1 | 22.31 | 0.77 | 2.20 | 1.71 | 25.97 | 7.84 | 1.72 |
| 151642 | 3 | 2 | 1 | 15.62 | 54.66 | 13.41 | 25.53 | 83.64 | 192.55 | 12.26 |
| 156730 | 3 | 1 | 2 | 31.07 | 1.29 | 2.83 | 2.39 | 18.88 | 7.14 | 1.67 |
| 15789 | 2 | 0 | 2 | 3.64 | 0.82 | 1.13 | 1.83 | 6.46 | 1.85 | 0.91 |
| 27465 | 2 | 1 | 1 | 6.63 | 0.06 | 3.52 | 1.52 | 17.43 | 2.36 | 1.80 |
| 61902 | 2 | 1 | 1 | 4.46 | 0.04 | 1.24 | 18.62 | 55.56 | 0.88 | 0.24 |
| 89107 | 2 | 1 | 1 | 2.15 | 0.24 | 0.99 | 3.39 | 25.75 | 1.31 | 0.24 |
| 101602 | 2 | 0 | 2 | 5.66 | 0.16 | 3.91 | 2.55 | 8.34 | 2.37 | 0.46 |
| 102323 | 2 | 1 | 1 | 7.60 | 2.51 | 1.30 | 2.38 | 22.01 | 5.07 | 1.18 |
| 102536 | 2 | 0 | 2 | 6.35 | 0.00 | 1.34 | 2.17 | 11.40 | 2.88 | 0.79 |
| 103109 | 2 | 0 | 2 | 1.48 | 0.08 | 0.93 | 1.28 | 8.55 | 2.11 | 1.36 |
| 129835 | 2 | 0 | 2 | 4.03 | 0.22 | 3.06 | 1.91 | 16.48 | 2.20 | 0.94 |
| 129880 | 2 | 1 | 1 | 4.15 | 0.19 | 0.49 | 8.15 | 19.67 | 4.32 | 1.04 |
| 151679 | 2 | 1 | 1 | 10.41 | 2.42 | 2.88 | 25.78 | 63.28 | 8.08 | 2.07 |

*Cutoff values for positivity of individual CB-CAP is: E-C4d (8.2), P-C4d (2.15), R-C4d 3.35), T-C4d (3.54), B-C4d (22.68), M-C4 (11.43), and G-C4d (3.59)

7 different CB-CAP assays performed on 32 individual patients. Abnormally elevated levels are shown in bold. Several observations can be made. First, all 11 samples from patients who have 5 or 4 C4 GCN are positive for both TC4d and BC4d. Second most of these patients are pan-positive for all seven of the CB-CAP assays. Third, of the 10 patients with a reduced number of 3 C4 GCN, only 3 of them have high levels of both TC4d and BC4d, and 7 are negative for both TC4d and BC4d or negative for one and borderline for the other. Fourth, 11 patients have a C4 GCN of 2 and only two of these patients are positive for both TC4d and BC4d. The other 9 are either double negative (7 patients) or negative and borderline (#89107; #129880). Fifth, many of the patients with <4 C4 GCN and negative TC4d and/or BC4d are positive for one of the other CB-CAPs in the panel. For example, #156730 C4 GCN=3) is negative for both TC4d and BC4d but positive for EC4d; #32958 (C4 GCN=3) is negative for both TC4d and BC4d but positive for both EC4d and MC4d; #97387 is negative for both TC4d and BC4d but positive for both EC4d and RC4d; #103323 (C4 GCN=2) is negative for both TC4d and BC4d but Example 4

Figure 5:
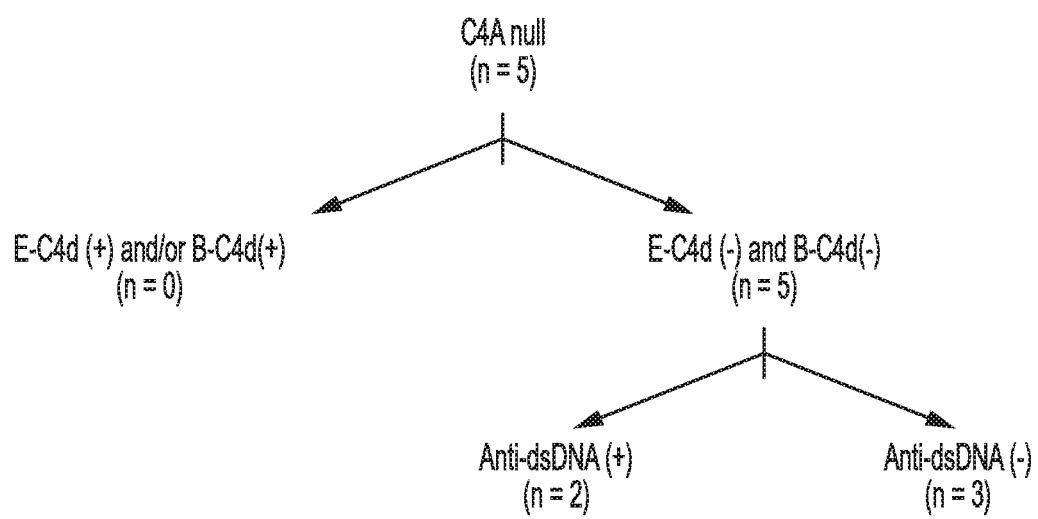
FIG. 5 presents a decision tree demonstrating laboratory test results in diagnosis of SLE for a set of example, anonymous patients.

An extreme condition regarding C4 GCN occurs when a patient has complete genetic deficiency of C4 i.e. a complete absence of functional C4A and C4B loci. This condition is extremely rare. However, more common, particularly in patients with lupus, is complete genetic deficiency of the C4A loci. FIG. 5 and Table 6 demonstrate laboratory test results for five such patients with lupus, all of whom were completely deficient in C4A. As shown in Table 6, all five of these patients diagnosed with lupus and determined to be completely deficient in C4A genetic loci, i.e. 0 functional loci (C4A null), were pan-negative when tested with a panel of 7 different CB-CAP assays. Three of the five were also negative for anti-dsDNA autoantibody testing one of the gold standards which is highly specific yet negative in the majority of patients with SLE at a given time point (FIG. 5). Together these data demonstrate that C4A-deficient individuals who are tested for CB-CAP levels with or without simultaneous determination of anti-dsDNA may be classified as non-lupus or non-pre lupus due to a false-negative result. Simultaneous determination of C4 GCN in these patients would demonstrate they are C4A null (C4A0) and indicate that CB-CAP assay results in these patients cannot be used or should be used with caution to diagnose lupus or pre-lupus due to the genetic deficiency.

TABLE 6

CB-CAP Levels of SLE Patients Who Have No C4A Genes (C4A Null)

| Patient ID | Total C4 GCN | C4A GCN | C4B GCN | E-C4d (SMFI) | P-C4d (SMFI) | R-C4d (SMFI) | T-C4d (SMFI) | B-C4d (SMFI) | M-C4d (SMFI) | G-C4d (SMFI) |
|---|---|---|---|---|---|---|---|---|---|---|
| 15789 | 2 | 0 | 2 | 3.64 | 0.82 | 1.13 | 1.83 | 6.46 | 1.85 | 0.91 |
| 134248 | 2 | 0 | 2 | 5.66 | 0.16 | 3.91 | 2.55 | 8.34 | 2.37 | 0.46 |
| 102536 | 2 | 0 | 2 | 6.35 | 0.00 | 1.34 | 2.17 | 11.40 | 2.88 | 0.79 |
| 103109 | 2 | 0 | 2 | 1.48 | 0.08 | 0.93 | 1.28 | 8.55 | 2.11 | 1.36 |
| 129835 | 2 | 0 | 2 | 4.03 | 0.22 | 3.06 | 1.91 | 16.48 | 2.20 | 0.94 |

This example demonstrates the value of C4 GCN testing for identification of patients with false negative determinations of EC4d, BC4d, other CB-CAPs and anti-dsDNA. Additional CB-CAP or other testing may be indicated for diagnosis, monitoring and/or stratification of such patients. This example demonstrates the CB-CAP phenotype of patients who are completely deficient in C4A. However, the data presented in the Tables provided herein collectively indicate that the absolute numbers of C4 GCN as well as the specific allotypes of C4 (i.e. both quantitative and qualitative determinations of C4 gene and proteins) may be important for accurate interpretation of CB-CAP values in a given individual.

Example 5

Figure 6:
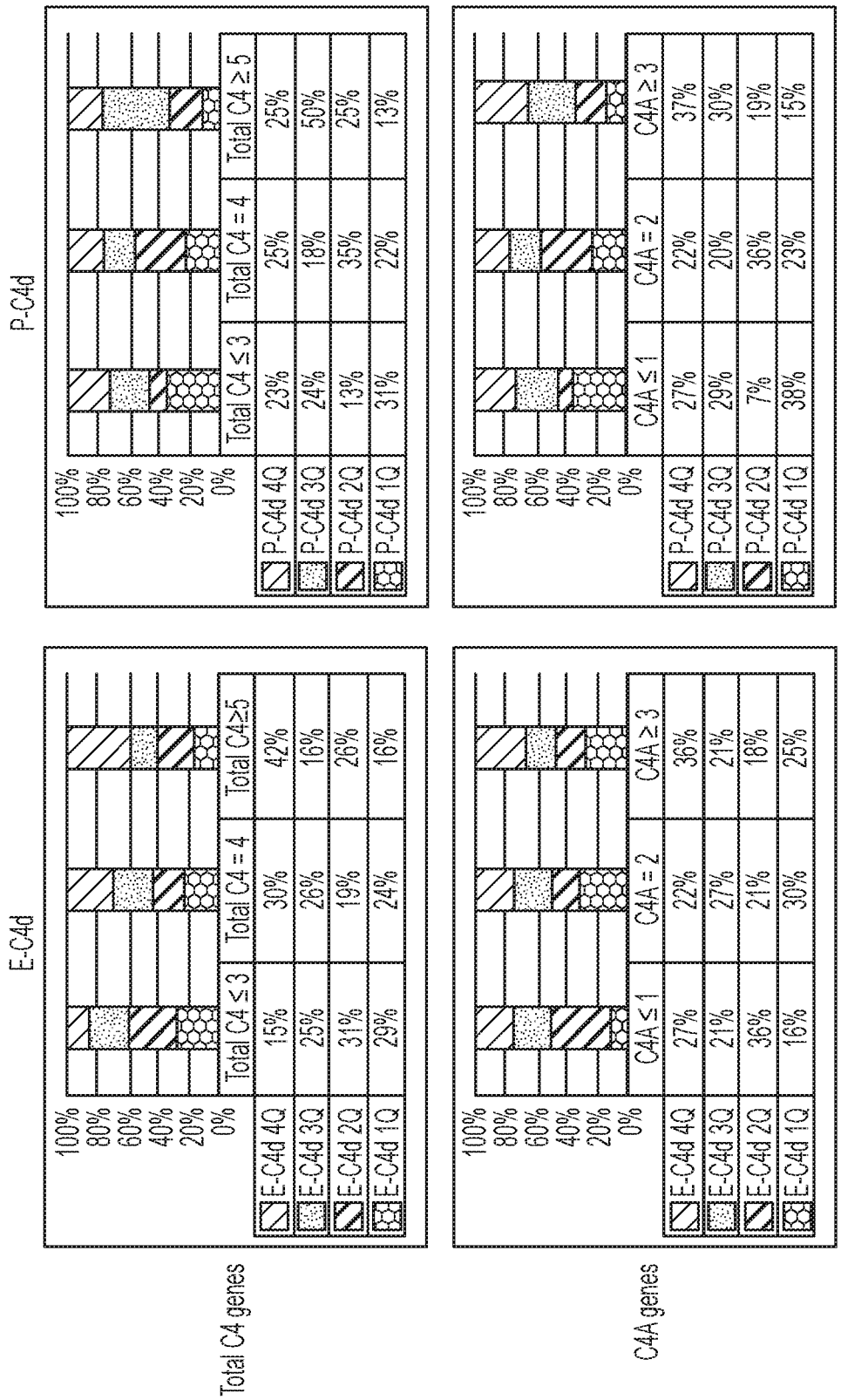
FIG. 6 presents tables illustrating a relationship between C4 gene copy numbers and E-C4d and P-C4d levels.
Figure 6:
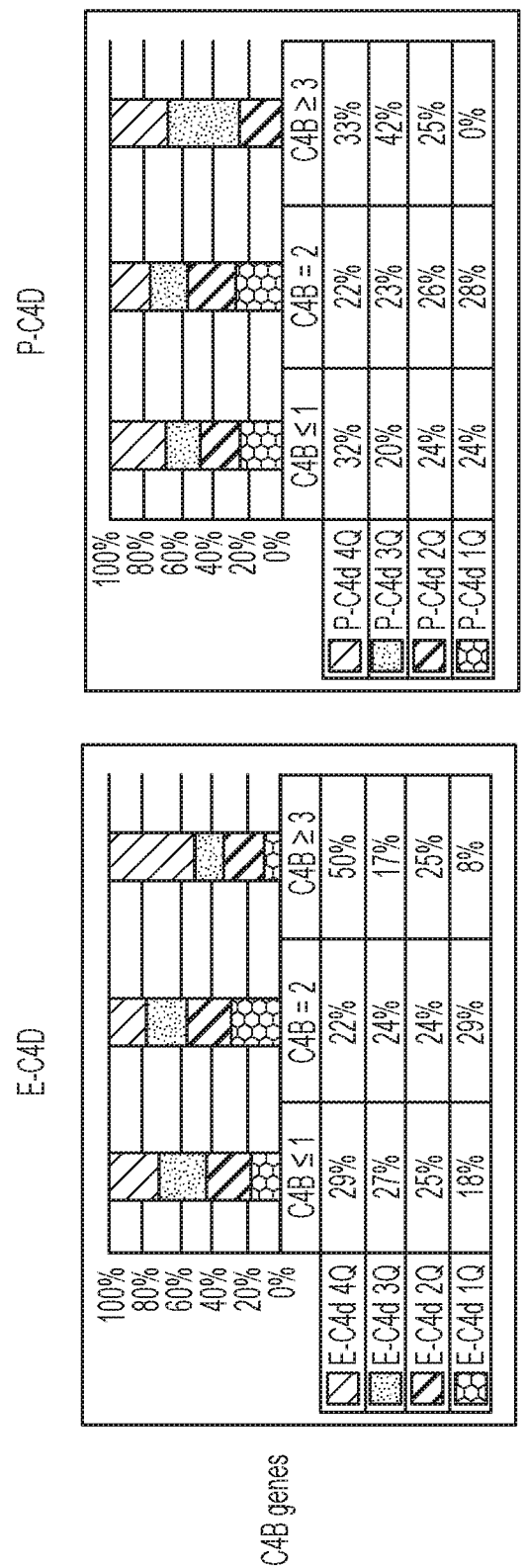
Figure 7:
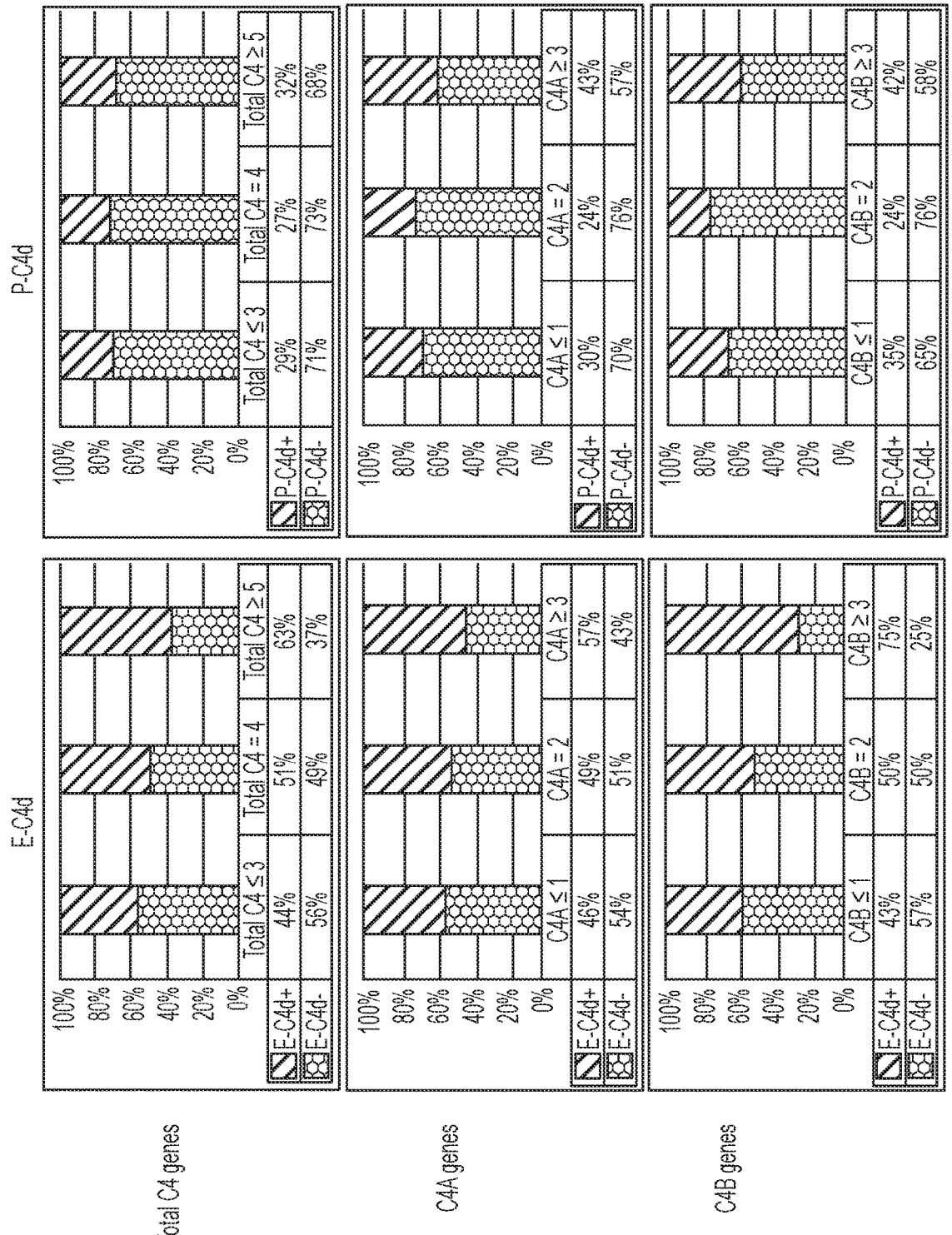
FIG. 7 presents tables illustrating a correlation between C4 gene copy numbers and E-C4d and P-C4d positivity.
Figure 8:
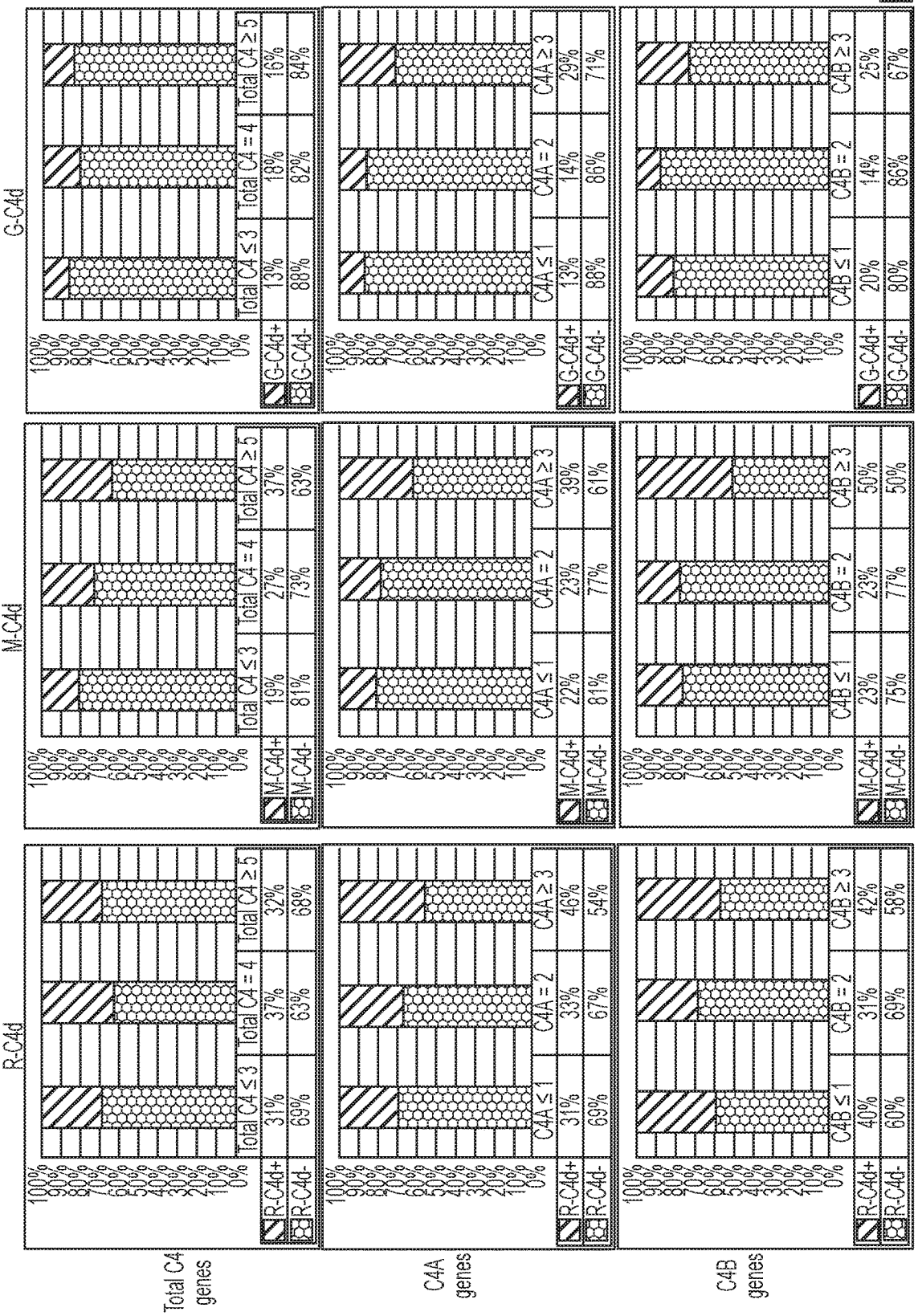
FIG. 8 presents tables illustrating a correlation between C4 gene copy numbers and R-C4d, M-C4d, and G-C4d positivity.

FIGS. 6, 7, and 8 demonstrate that CB-CAP levels of EC4d, PC4d, RC4d, MC4d and GC4d may not be influenced by C4 GCN to the same extent as are TC4d and BC4d.

Erythrocyte C4d (EC4d), and Platelet C4d (PC4d) levels do not appear to be influenced by C4 GCN to the same extent as are TC4d and BC4d, as represented in FIGS. 6 and 7.

For the analyses shown in FIG. 6, SLE patients were divided into quartiles based on either E-C4d levels or P-C4d levels. The copy numbers of total C4 genes (C4A and C4B), C4A genes, and C4B genes of individual patients were determined as described above in Example 1. The distribution of patients with different C4GCNs in the E-C4d/P-C4d quartile scales was plotted. Fisher's exact test or Chi-square test was performed to determine the statistical significance of this trend. The p values for the correlation between E-C4d and total C4 GCN, E-C4d and C4A GCN, and E-C4d and C4B GCN, were 0.119, 0.063, and 0.206, respectively. The p values for the correlation between P-C4d and total C4 GCN, P-C4d and C4A GCN, and P-C4d and C4B GCN, were also not significant.

For the analyses shown in FIG. 7, SLE patients were divided into binary groups based on E-C4d or P-C4d positivity. The copy numbers of total C4 genes (C4A and C4B), C4A genes, and C4B genes of individual patients were determined as described in Example 1. The distribution of patients with different C4GCNs in the E-C4d/P-C4d positive and negative group was plotted. Fisher's exact test or Chi-square test was performed to determine the statistical significance of this trend. The p values for the correlation between E-C4d positivity and total C4 GCN, E-C4d and C4A GCN, and E-C4d and C4B GCN, were 0.27, 0.65, and 0.14, respectively. The p values for the correlation between P-C4d and total C4 GCN, P-C4d and C4A GCN, and P-C4d and C4B GCN, were 0.87, 0.14, and 0.19 respectively.

For the analyses shown in FIG. 8, SLE patients were divided into binary groups based on R-C4d, M-C4d, and G-C4d positivity. The copy numbers of total C4 genes (C4A and C4B), C4A genes, and C4B genes of individual patients were determined as described in Example 1. The distribution of patients with different C4 GCNs in the R-C4d positive and R-C4d negative groups, M-C4d positive and M-C4d negative groups, and G-C4d positive and G-C4d negative groups, was plotted. Fisher's exact test or Chi-square test was performed to determine the statistical significance of this trend. The p values for the correlation between R-C4d positivity and total C4 GCN, R-C4d and C4A GCN, and R-C4d and C4B GCN, were 0.71, 0.41, and 0.48, respectively. The p values for the correlation between M-C4d positivity and total C4 GCN, M-C4d and C4A GCN, and M-C4d and C4B GCN, were 0.19, 0.16, and 0.11, respectively. The p values for the correlation between G-C4d positivity and total C4 GCN, G-C4d and C4A GCN, and G-C4d and C4B GCN, were 0.55, 0.13, and 0.41, respectively.

Additional analyses are described below.

Reticulocyte C4d (R-C4d): SLE patients were divided into binary groups based on R-C4d positivity. The copy numbers of total C4 genes (C4A and C4B), C4A genes, and C4B genes of individual patients were determined as described above. The distribution of patients with different C4 GCNs in the R-C4d positive and negative group was plotted. Fisher's exact test or Chi-square test was performed to determine the statistical significance of this trend. The p values for the correlation between R-C4d positivity and total C4 GCN, R-C4d and C4A GCN, and R-C4d and C4B GCN, were 0.71, 0.41, and 0.48, respectively.

Monocyte C4d (M-C4d): SLE patients were divided into binary groups based on M-C4d positivity. The copy numbers of total C4 genes (C4A and C4B), C4A genes, and C4B genes of individual patients were determined as described above. The distribution of patients with different C4 GCNs in the M-C4d positive and negative group was plotted. Fisher's exact test or Chi-square test was performed to determine the statistical significance of this trend. The p values for the correlation between M-C4d positivity and total C4 GCN, M-C4d and C4A GCN, and M-C4d and C4B GCN, were 0.19, 0.16, and 0.11, respectively.

Granulocyte C4d (G-C4d): SLE patients were divided into binary groups based on G-C4d positivity. The copy numbers of total C4 genes (C4A and C4B), C4A genes, and C4B genes of individual patients were determined as described above. The distribution of patients with different C4 GCNs in the G-C4d positive and negative group was plotted. Fisher's exact test or Chi-square test was performed to determine the statistical significance of this trend. The p values for the correlation between G-C4d positivity and total C4 GCN, G-C4d and C4A GCN, and G-C4d and C4B GCN, were 0.55, 0.13, and 0.41, respectively.

These results support the potential value of using these CB-CAPs as secondary assays in patients who are TC4d and/or BC4d normal, or less than diagnostic for lupus/pre-lupus, in the presence of reduced C4 GCN. Together these data suggest that determination of a panel of CB-CAP assays in the context of C4 GCN may be useful for personalized (precision) medicine in the diagnosis and monitoring of patients with lupus and/or pre-lupus.

In various embodiments, some or all of the steps described above may be performed by an electronic device that is executing programming instructions. For example, the steps of determining and extracting control levels or baselines, accessing other data sets, comparing a subject's levels to the control levels, and/or generating reports all may be done by an electronic device. For the purposes of this document, an "electronic device" or "processing device" refers to a device or a system of one or more devices that includes or has access to a processor and a non-transitory, computer-readable memory. The memory may be integral to the device, or it may be remote from the device and accessible by the device via one or more communication networks. The memory may contain programming instructions that, when executed by the processor, are configured to cause the processor to perform one or more operations according to the programming instructions. Examples of electronic devices include computing devices, tablets, and smart phones.

When used in this document, the term "processor" can refer to a single processor or to multiple processors that together implement various steps of a process. Similarly, a "memory device" or "database" can refer to a single device or databases or multiple devices or databases across which programming instructions and/or data are distributed.

The disclosure of the following patent documents are incorporated herein by reference: U.S. Pat. No. 8,126,654, issued Feb. 28, 2012, titled "Identification and Monitoring of Systemic Lupus Erythematosus"; U.S. Pat. No. 7,390,631, issued Jun. 24, 2008, titled "Diagnosis and Monitoring of Systemic Lupus Erythematosus and of Scleroderma"; U.S. Pat. No. 9,495,517, issued Nov. 15, 2016, titled "Cell-Bound Complement Activation Products as Diagnostic Biomarkers for Pre-Lupus"; United States Patent Application Number 2017/0067893, published Mar. 9, 2017, titled "Cell-Bound Complement Activation Products as Diagnostic Biomarkers for Pre-Lupus" and United States Patent Application Number 2016/0041164, published Feb. 11, 2016, titled "Anti-Lymphocyte Autoantibodies As Diagnostic Biomarkers".

The features and functions described above, as well as alternatives, may be combined into many other different systems or applications. Various alternatives, modifications, variations or improvements may be made by those skilled in the art, each of which is also intended to be encompassed by the disclosed embodiments.

All references cited herein are incorporated by reference herein in their entireties.

The invention claimed is:

1. A method of obtaining one or more corrected cell-bound complement activation product (CB-CAP) levels for a blood sample from a patient, the method comprising:
(a) measuring the number of C4 gene copies in a genomic DNA sample from the patient and detecting a reduced number of C4 gene copies in a genomic DNA sample from the patient compared to a C4 gene copy number threshold value;
(b) performing one or more cell-bound complement activation product (CB-CAP) assays on a blood sample from the patient to generate blood sampling data for the patient, wherein the one or more CB-CAP assays comprise a panel of assays using monoclonal antibodies specifically reactive with at least one of the following CB-CAPs: E-C4d, R-C4d, T-C4d, B-C4d, M-C4d, G-C4d, P-C4d, Eos-C4d, and Baso-C4d, and wherein the blood sampling data comprises one or more CB-CAP levels for one or more CB-CAPs in the patient;
(c) detecting that the one or more CB-CAP levels for the patient are not elevated as compared to a control; and
(d) multiplying one or more of the one or more CB-CAP levels for the patient by a correction factor to obtain one or more corrected CB-CAP levels for the patient.

2. The method of claim 1, the method further comprising:
(a) detecting that the one or more corrected CB-CAP levels for the patient are elevated as compared to the control; and
(b) using the one or more corrected CB-CAP levels for the patient that are elevated in a determination of whether the patient has lupus or pre-lupus.

3. The method of claim 1, comprising detecting a reduced number of C4 gene copies in a genomic DNA sample by a Southern blot assay, a qPCR assay, or DNA sequencing.

4. The method of claim 1, wherein the one or more CB-CAP levels comprise measurements for one or more selected from the group consisting of T-C4d, B-C4d, and E-C4d.

5. The method of claim 2, wherein the CB-CAPs for which one or more corrected CB-CAP levels are elevated as compared to the control include T-C4d, B-C4d, or both.

6. The method of claim 5, wherein the CB-CAPs for which one or more corrected CB-CAP levels are elevated as compared to the control include one or more of E-C4d, R-C4d, P-C4d, and M-C4d.

7. The method of claim 1, wherein identifying the correction factor comprises one or more of the following:
(a) identifying a multiplier equal to a ratio of a mean normal C4 gene copy number to the patient's reduced C4 gene copy number;
(b) accessing a table of correction factors and selecting, from the table, a correction factor that is associated with a CB-CAP; or
(c) using a standard correction factor that is also used for other patients.

8. The method of claim 1, wherein the number of C4 gene copies comprises a C4A gene copy number, a C4B gene copy number, or both.

9. The method of claim 1, wherein determining the C4 gene copy number threshold value comprises:
(a) identifying a mean or median gene copy number for a segment of patients in a control; and
(b) setting the C4 gene copy number threshold equal to one or more standard deviations from the identified mean or median gene copy number.

10. The method of claim 2, wherein each instance of determining that the patient has lupus or pre-lupus comprises:
(a) if the patient meets at least a threshold level of classification criteria for lupus, determining that the patient has lupus; and (b) if the patient does not meet at least the threshold level of classification criteria for lupus but meets at least one of the criteria, determining that the patient has pre-lupus.

11. The method of claim 10, wherein the classification criteria are selected from the group consisting of serositis; oral ulcers; arthritis; photosensitivity; blood disorders; renal involvement; antinuclear antibodies; immunologic phenomena; neurologic disorder; malar rash; and discoid rash.

\* \* \* \* \*